United States Patent
Raynal et al.

(10) Patent No.: US 10,350,184 B2
(45) Date of Patent: Jul. 16, 2019

(54) DERIVATIVES USED IN THE TREATMENT OF MUSCLE ATROPHY

(71) Applicant: METABRAIN RESEARCH, Chilly Mazarin (FR)

(72) Inventors: Sophie N. Raynal, Paris (FR); Micheline R. Kergoat, Les Ulis (FR); Valerie Autier, Gif sur Yvette (FR); Christine G. Charon, Gometz le Chantel (FR); Jean-Denis Durand, Montreuil Sous Bois (FR); Franck F. Lepifre, Saclay (FR); Annick M. Audet, Leudeville (FR)

(73) Assignee: METABRAIN RESEARCH, Chilly Mazarin (FR)

( * ) Notice: Subject to any disclaimer, the term of this patent is extended or adjusted under 35 U.S.C. 154(b) by 0 days.

(21) Appl. No.: 15/566,955

(22) PCT Filed: Apr. 14, 2016

(86) PCT No.: PCT/FR2016/050864
§ 371 (c)(1),
(2) Date: Feb. 21, 2018

(87) PCT Pub. No.: WO2016/166480
PCT Pub. Date: Oct. 20, 2016

(65) Prior Publication Data
US 2018/0303780 A1    Oct. 25, 2018

(30) Foreign Application Priority Data
Apr. 16, 2015 (FR) .................. 15 53410

(51) Int. Cl.
| | |
|---|---|
| *A61K 31/15* | (2006.01) |
| *A61K 31/50* | (2006.01) |
| *A61P 21/00* | (2006.01) |
| *A61K 31/165* | (2006.01) |
| *A61K 31/197* | (2006.01) |
| *A61K 31/216* | (2006.01) |
| *A61K 31/495* | (2006.01) |
| *A61K 31/4402* | (2006.01) |
| *A61K 31/4406* | (2006.01) |

(52) U.S. Cl.
CPC ............ *A61K 31/197* (2013.01); *A61K 31/15* (2013.01); *A61K 31/165* (2013.01); *A61K 31/216* (2013.01); *A61K 31/4402* (2013.01); *A61K 31/4406* (2013.01); *A61K 31/495* (2013.01); *A61K 31/50* (2013.01); *A61P 21/00* (2018.01)

(58) Field of Classification Search
CPC combination set(s) only.
See application file for complete search history.

(56) References Cited

U.S. PATENT DOCUMENTS

| | | | |
|---|---|---|---|
| 2002/0161050 A1 | 10/2002 | Purchase et al. | |
| 2008/0019915 A1* | 1/2008 | Hadida-Ruah | C07D 405/12 424/9.2 |

FOREIGN PATENT DOCUMENTS

| | | | | |
|---|---|---|---|---|
| FR | 2204406 | | 5/1974 | |
| FR | 2204406 A1 * | | 5/1974 | ......... C07D 295/185 |
| WO | 9809940 | | 3/1998 | |
| WO | 2010011302 | | 1/2010 | |
| WO | WO-2010011302 A1 * | | 1/2010 | ........... C07C 251/48 |
| WO | WO-2017044551 A1 * | | 3/2017 | ............ A61K 31/00 |

OTHER PUBLICATIONS

International Osteoporosis Foundation "Treating Sarcopenia" 2017 [online][retrieved on Sep. 24, 2018]. Retrieved from <https://www.iofbonehealth.org/treating-sarcopenia>. (Year: 2017).*

Sakai et al. "Lipase-Catalyzed Resolution of (2R*,3S*)- and (2R*,3R*)-3-Methyl-3-phenyl-2-aziridinernethanol at Low Temperatures and Determination of the Absolute Configurations of the Four Stereoisomers" J. Org. Chem. 2005, 70, 1369-1375. (Year: 2005).*

(Continued)

*Primary Examiner* — Amanda L Aguirre
(74) *Attorney, Agent, or Firm* — Hamre, Schumann, Mueller & Larson, P.C.

(57) ABSTRACT

This invention relates to oxime and alkoxy derivatives of the general formula (I), (I)

Figure 1:
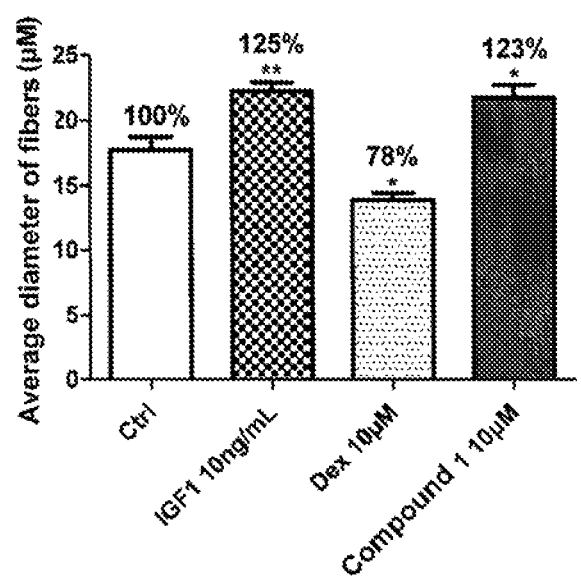

or an enantiomer, diastereoisomer, hydrate, solvate, tautomer, racemic mixture or pharmaceutically acceptable salt thereof for use as a medicament for the treatment and/or prevention of muscle atrophy in mammals and/or for limiting muscular atrophy in mammals and/or to promote muscle growth in exercising mammals aimed at increasing muscle mass and quality, preventing the occurrence of symptoms of sarcopenia related to age or rehabilitation after a muscle loss, age-related muscle atrophy and/or the consequences of drug therapy and/or immobilization and/or cachexia.

13 Claims, 1 Drawing Sheet
Specification includes a Sequence Listing.

(56) References Cited

OTHER PUBLICATIONS

International Search Report issued in International Application No. PCT/FR2016/050864 dated Sep. 12, 2016 (6 pages).
Written Opinion issued in International Application No. PCT/FR2016/050864 dated Sep. 12, 2016 (5 pages).
Vellas et al.: "A Two-Year Longitudinal Study of Falls in 482 Community-Dwelling Elderly Adults"; Journal of Gerontology, Medical Sciences, 1998, vol. 53A, pp. M264-M274.
Chai et al.: "Striking Denervation of Neuromuscular Junctions without Lumbar Motoneuron Loss in Geriatric Mouse Muscle"; PLOS One, 2011, vol. 6, pp. 1-11.
Farnfield et al.: "Activation of mTOR signalling in young and old human skeletal muscle in response to combined resistance exercise and . . . "; Applied Physiology Nutrition and Metabolism, 2012, pp. 1; 21-30 (11 pages).
Frontera et al.: "A cross-sectional study of muscle strenght and mass in 45 to 78-yr-old men and women"; Human Physiology Laboratory, 1991, pp. 644-650.
Se-Jin Lee: "Extracellular Regulation of Myostatin: A Molecular Rheostat for Muscle Mass"; Immunol Endocr Metab Agents Med Chem, 2010, vol. 10, pp. 183-194.
Leger et al.: "Human Sarcopenia Reveals an Increase in SOCS-3 and Myostatin and a Reduced Efficiency of Akt Phosphorylation"; Rejuavenation Research, 2008, vol. 11, pp. 163-175B.
Li et al.: "Myostatin Directly Regulates Skeletal Muscle Fibrosis"; Journal of Biological Chemistry, 2008, vol. 283, No. 28, pp. 19371-19378.
Lloyd et al.: "Recurrent and Injurious Falls in the Year Following Hip Fracture: A Prospective Study of Incidence and Risk Factors From the Sarcopenia and Hip Fracture Study"; Journal of Gerontology, Medical Sciences, 2009, vol. 64A, pp. 599-609.
McPherron et al.: "Double muscling in cattle due to mutations in the myostatin gene"; Proc. Natl. Acad, Sci, 1997, vol. 94, pp. 12457-12461.
McPherron et al.: "Suppression of body fat accumulation in myostatin-deficient mice"; Department of Molecular Biology and Genetics, Journal of Clinical Investigation, 2002, vol. 109, pp. 595-601.
John E. Morley: "Weight Loss in Older Persons: New Therapeutic Approaches"; Current Pharmaceutical Design, 2007, vol. 13, pp. 3637-3647.
O'Neill et al: "Absence of insulin signalling in skeletal muscle is associated with reduced muscle mass and function: evidence for decreased protein synthesis and not increased degradation"; Age, 2010, vol. 32, pp. 209-222.
Wolfman et al.: "Activation of latent myostatin by the BMP-1 / tolloid family of metalloproteinases"; PNAS, 2003, vol. 100, pp. 15842-15846.
Bass et al.: "Growth factors controlling muscle development", Domestic Animal Endocrinology, 1999, vol. 17, pp. 191-197.
Hasselgren et al.: "Molecular Regulation of Muscle Cachexia: It May Be More Than the Proteasome"; Biochemical and Biophysical Research Communications, 2002, vol. 290, pp. 1-10.
Purintrapiban et al: "Degradation of sarcomeric and cytoskeletal proteins in cultured skeletal muscle cells"; Comparative Biochemistry and Physiology Part B, 2003, vol. 136, pp. 393-401.
Thies et al.: "GDF-8 Propeptide Binds to GDF-8 and Antagonizes Biological Activity by Inhibiting GDF-8 Receptor Binding"; Growth Factors, 2001, pp. 251-259.

* cited by examiner

SEQUENCE LISTING

<160> NUMBER OF SEQ ID NOS: 6

<210> SEQ ID NO 1
<211> LENGTH: 22
<212> TYPE: DNA
<213> ORGANISM: artificial sequence
<220> FEATURE:
<223> OTHER INFORMATION: primer

<400> SEQUENCE: 1
gagtctgact ttctaatgca ag                                    22

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
tgttgtagga gtcttgacgg                                       20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
agagtcggca agtctgtgct                                       20

<210> SEQ ID NO 4
<211> LENGTH: 19
<212> TYPE: DNA
<213> ORGANISM: artificial sequence
<220> FEATURE:
<223> OTHER INFORMATION: primer

<400> SEQUENCE: 4
gtgaggcctt tgaaggcag                                        19

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
ctctagactt cgagcaggag                                       20

```
<210> SEQ ID NO 6
<211> LENGTH: 19
<212> TYPE: DNA
<213> ORGANISM: artificial sequence
<220> FEATURE:
<223> OTHER INFORMATION: primer

<400> SEQUENCE: 6
ggtaccacca gacagcact                                              19
```

DERIVATIVES USED IN THE TREATMENT OF MUSCLE ATROPHY

DESCRIPTION OF THE INVENTION

This invention relates to derivatives useful for the treatment of diseases related to muscle atrophy.

FIELD OF THE INVENTION

Today there is a clear lack of new treatments to delay the onset and progression of age-related disorders and diseases that are accompanied by a decrease in muscle strength or power such as sarcopenia while mobility problems linked to aging are very serious problems with far-reaching health consequences.

Elderly people with certain metabolic disorders or diseases are most often faced with a loss of lean body mass due at least in part to a reduction in muscle protein synthesis (such as sarcopenia), a decrease in nutritional intake, or the presence of inflammation. A decrease in lean body mass is known to be associated with fatigue, a decreased ability to perform the tasks required for daily living, increased risk of bone fractures, an increase in falls and hospitalizations, impaired metabolism (glucose tolerance, insulin sensitivity) and in cognitive, capacity as well as decreased quality of life (Frontera W R et. al., 1991, Baumgartner et al., 1998, Lloyd B D et al., 2009). Unlike cachexia, patients with sarcopenia can have a stable weight, but show a clear loss of muscle mass, while typically at the same time the fat mass increases.

Many factors influence the decrease in muscle mass. Essentially, an anabolic resistance of skeletal muscle to protein synthesis is observed as can be seen in an immobilization which can be improved at least in part by resistance exercise and dietary supplementation (Farnfield M M et. al. 2012). It has also been shown that loss of innervation and oxidative damage may play an important role (Chai R J et al., 2011, O'Neill E D et al., 2010) and lead to muscle atrophy involving different cell signaling pathways, while also leading to programmed cell death (apoptosis), increased protein degradation, or even decreased activation of the cells responsible for muscle regeneration. Sarcopenia is therefore the result of an imbalance between the degradation of proteins and their synthesis, where the exact contribution of each of the factors mentioned above varies according to the model or case studied. Some proteolytic systems have been described as participating in muscle breakdown such as calcium-activated proteases such as calpain and caspases; the ubiquitin-proteasome system (Hasselgren P O et al, 2002, Purintrapiban J et al., 2003). Among the different targets identified during the development of sarcopenia, atrogin-1 (also known as MATbx) and MURF-1 were found to be increased and Akt/mTOR/S6K decreased.

Autocrine produced myostatin, produced by the muscles themselves, is also a particularly important factor, as this protein acts both by stimulating proteolysis and inhibiting proteosynthesis. While aging is accompanied by significant hormonal changes, there is an increased secretion of myostatin (Léger et al., 2008) whose expression in adult muscles increases with the degree of atrophy. Myostatin, also known as growth and differentiation factor-8 (GDF-8) has all the structural features common to TGF-β family proteins: a hydrophobic aminoterminal that acts as a secretory signal, nine invariant cysteine residues, and a Turin proteolytic processing site, "RXXR". Proteolytic cleavage of the protein results in a C-terminal domain that forms a homodimer that is the biologically active form of myostatin (Thies et al., 2001). Amino acid sequence alignments of myostatin from multiple vertebrate species indicate that the protein is highly conserved (100% identity) between humans, apes, cows, dogs, mice, rats, turkey and chicken (McPherron et al., 1997). Its expression is limited primarily to skeletal muscle and adipose tissue, where it plays the role of a negative regulator of skeletal muscle development (Lee L S, 2010, 10:183-194).

Mice and cattle that are genetically deficient in myostatin have been shown to exhibit dramatic increases in skeletal muscle mass, thus supporting the role of myostatin in suppressing muscle growth (Wolfram et. al., 2003). In some bovine breeds, muscle hypertrophy is due to a missense mutation in the third exon of the bovine myostatin gene (Bass et al., 1999) which is accompanied by an increase in both the number of cells or hyperplastic growth, and cell size, or hypertrophic growth, resulting in larger and heavier myofibers.

Increased skeletal muscle mass and strength are also associated with metabolic adaptations that positively influence body composition, energy expenditure, glucose homeostasis, and insulin requirements. Pharmacological and genetic data indicate that myostatin regulates energy metabolism and that its inhibition can significantly reduce the progression of metabolic diseases such as obesity and diabetes. For example, mice genetically deficient in myostatin have low body fat accumulation (MePherron et al., 2002) compared to wild-type mice of the same age, related to a reduction in adipocyte count and size, demonstrating thus the important role of myostatin in adipogenesis, and myogenesis.

The current experimental treatments for Sarcopenia rely on nutritional approaches, physical exercise, the use of appetite stimulants or anabolic compounds such as testosterone, but the effects of these treatments are not satisfactory (Morley et al, 2007) and may cause side effects. This invention relates to derivatives and the pharmaceutical compositions comprising them for use in the treatment and/or prevention of muscle atrophy in mammals.

DETAILED DESCRIPTION OF THE INVENTION

This invention therefore relates to derivatives of the following general formula I:

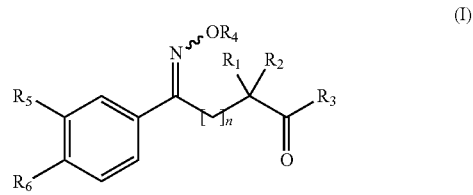

in which
$R^1$ and $R^2$ independently from each another are a hydrogen molecule or ($C_1$-$C_6$) alkyl, preferably a methyl;
n is an integer between 1 and 2, preferably n=1;
$R^3$ represents
  an —OH group;
  an —O($C_1$-$C_6$ alkyl) group, advantageously —OEt or —OiPr;
  an —O ($C_3$-$C_6$ cycloalkyl) group, advantageously an —O-cyclopentyl;

an —O ($C_3$-$C_7$ heterocyclic) group, advantageously an —O-tetrahydropyran-4-yl;
an —O-heteroaryl group, advantageously an —O-pyridyl;
an —O-aryl group, advantageously an —O-phenyl;
an —O($C_1$-$C_6$ alkyl) amyl group, advantageously an —O-benzyl;
an —$NR^7R^8$ group, in which
$R^7$ represents a hydrogen atom or a $C_1C_6$ alkyl group and $R^8$ represents
  a hydrogen atom;
  a heteroaryl group, advantageously containing one or more nitrogen atoms, in particular a pyridazinyl group or a pyridyl group;
  a $C_1$-$C_6$ alkyl group, advantageously an ethyl group, optionally substituted with an $NR^9R^{10}$ group in which $R^9$ and $R^{10}$ represent, independently from each another, a hydrogen atom or a $C_1$-$C_6$ alkyl group, advantageously a group methyl;
a $C_1$-$C_6$ alkyl group, advantageously an ethyl group, optionally substituted with a group —$OR^{11}$ in which $R^{11}$ represents a hydrogen atom or a $C_1$-$C_6$ alkyl group, advantageously a methyl group;
or $R^7$ and $R^8$ forming with the nitrogen atom which provides them with a heterocycle, in particular a pyrrolidine, a piperidine, a morpholine, a piperazine, the heterocycle being optionally substituted by a $C_1$-$C_6$ alkyl group, advantageously a methyl group, in particular $R^7$ and $R^8$ form a methylpiperazinyl;
$R^4$ represents a hydrogen atom or a $C_1$-$C_6$ alkyl group, in particular -Me or -Et, more particularly -Et;
$R^5$ and $R^6$ represent, independently from each another, a hydrogen, a halogen atom, advantageously Cl, or a group chosen from:
a —CN group;
an —OH group;
an —O($C_1$-$C_6$ alkyl) group, advantageously —OMe, the alkyl group being optionally substituted by one or more halogen atoms, advantageously F, such as for example —$OCF_3$ or —$OCHF_2$;
a $C_1$-$C_6$ alkyl group, advantageously methyl, optionally substituted by one or more halogen atoms, advantageously F, such as for example —$CF_3$, an —O($C_3$-$C_6$ cycloalkyl) group, advantageously O-cyclopropyl;
or an enantiomer, diastereoisomer, hydrate, solvate, tautomer, racemic mixture or pharmaceutically acceptable salt thereof
for use as a medication for the treatment and/or prevention of muscle atrophy in mammals and/or for limiting muscle atrophy in mammals and/or for promoting mammalian muscle enhancement, min mammals who exercise and aiming to increase muscle mass and quality, preventing the appearance of age-related symptoms of sarcopenia or rehabilitation after muscle loss,
muscle atrophy that is related to age and/or the consequences of drug therapy and/or immobilization and/or cachexia.

In particular, muscle atrophy is age-related, such as pre-sarcopenia sarcopenia, or severe sarcopenia. Muscle atrophy can also be related to the consequences of drug treatment, such as cancer treatment. Muscle atrophy may also be related to immobilization, particularly regardless of the cause, for example due to age-related weakness, accident or surgery, such as a prosthesis of the knee or the hip. Lastly, muscle atrophy may be related to cachexia, in particular whatever the cause, for example due to anorexia nervosa, cancer, heart failure, liver failure, insufficiency kidney, tuberculosis or AIDS.

Specifically, the mammal may be an animal or man, advantageously it would be man.

According to this invention, the derivatives of formula (I) thus have an activity for the treatment and/or the prevention of muscle, atrophy, in particular, age-related muscle atrophy, such as pre-sarcopenia sarcopenia, or severe sarcopenia, and/or related to the consequences of drug treatment such as a cancer treatment, and/or related to immobilization, in particular whatever the cause, such as for example the weakness related to age, an accident, a surgical operation such as the installation of a prosthesis of the knee or the hip, cachexia, and in general, pathologies related to muscle atrophy in mammals.

The derivatives of formula (I) are also useful for promoting the muscular growth in mammals, especially of human beings, by exercising and aiming to increase the mass and the quality of muscles, for example by preventing the appearance of symptoms of sarcopenia related to age.

The inventors have discovered that the derivatives according to this invention make it possible, to inhibit gene expression of my-ostatin, to increase protein synthesis in muscle cells and/or to increase the diameter of myotubes in C2Cl2 cells.

This invention further relates to the use of a derivative of formula (I) according to the invention as defined above for the manufacture of a medication fix the treatment and/or prevention of muscle atrophy in mammals and/or to limit muscle atrophy in mammals and/or to promote the muscle growth in mammals who exercise and aiming to increase the mass and quality muscle, in order to prevent the appearance of symptoms of sarcopenia related to age or rehabilitation after muscle loss.

It also relates to a method of treatment and/or prevention and/or prophylactic treatment and/or to delay the onset of muscle atrophy in mammals and/or for limiting muscle atrophy in mammals and/or to promote the muscle growth of mammals who exercise and aiming to increase the mass and quality of muscle, preventing the appearance of age-related symptoms of sarcopenia or rehabilitation following muscle loss including the administration of an effective amount of a derivative of formula (I) according to the invention to a subject in need thereof.

The effective amount will be adapted according to the nature and severity of the pathology to be, treated, the route of administration and also the weight and age of the subject. In general, the dosage unit will vary between 0.5 mg and 2000 mg per day, in one or more doses, preferably between 1 and 1000 mg when the subject is human.

In an advantageous embodiment, the derivatives of formula (I) useful in the context of this invention are such that $R^4$ represents a —($C_1$-$C_6$) alkyl group, advantageously -Et.

In another advantageous embodiment, the derivatives of formula (I) useful in the context of this invention are such that n=1;

In yet another advantageous embodiment, the derivatives of formula (I) useful in the context of the present invention are such that the groups $R^5$ and/or $R^6$ represent a halogen atom, advantageously a chlorine atom.

In yet another advantageous embodiment, the derivatives of formula (I) useful in the context of the present invention are such that $R^5$ and $R^6$ represent, independently of each another, a halogen atom, advantageously Cl; particularly $R^5$ and $R^6$ are chlorines, and $R^4$ is a $C_1$-$C_6$ alkyl group, in particular Et.

In another advantageous embodiment, the derivatives of formula (I) useful in the context of this invention are such that $R^1$ and $R^2$ both represent a hydrogen atom.

In yet another advantageous embodiment, the derivatives of formula (I) useful in the context of this invention are such that $R^3$ represents an —OH group or an —O($C_1$-$C_6$ alkyl) group, advantageously —OEt or —OiPr.

In particular, the derivatives of formula (I) useful in the context of this invention are chosen from the following compounds.
(1) 4-(3,4-dichlorophenyl)-4-ethoxyimino-butanoic acid;
(2) 4-(3,4-dichlorophenyl)-4-methoxyimino-butanoic acid;
(3) Isopropyl 4-(3,4-dichlorophenyl)-4-ethoxyimino-butanoate;
(4) 5-(3,4-dichlorophenyl)-5-ethoxyimino-pentanoic acid;
(5) 4-(3,4-dichlorophenyl)-4-ethoxyimino-N-(2-pyridyl) butanamide;
(6) 4-(3,4-dichlorophenyl)-4-ethoxyimino-N-(3-pyridyl) butanamide;
(7) 4-(3,4-dichlorophenyl)-4-ethoxyimino-N-pyridazin-3-yl-butanamide;
(8) 4-(3,4-dichlorophenyl)-N-(2-dimethylaminoethyl)-4-ethoxyimino-butanamide;
(9) (4E)-4-(3,4-dichlorophenyl)-4-ethoxyimino-N-(3-hydroxypropyl) butanamide;
(10) 4-(3,4-dichlorophenyl)-4-ethoxyimino-1-(4-methylpiperazin-1-yl) butan-1-one;

In particular, the following compounds (1 to 10) which are covered by the general formula (I) are described in the Prior Art for other applications:

| No. | Chemical Structure | Chemical Name |
|---|---|---|
| 1 | 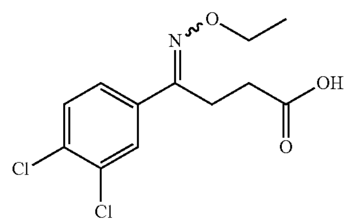 [SMILES: CCON=C(CCC(=O)O)c1ccc(Cl)c(Cl)c1] | 4-(3,4-dichlorophenyl)-4-ethoxyimino-butanoic acid |
| 2 | 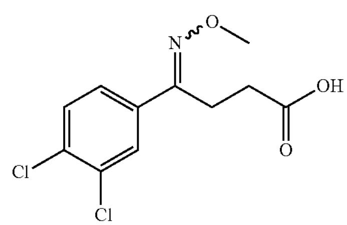 [SMILES: CON=C(CCC(=O)O)c1ccc(Cl)c(Cl)c1] | 4-(3,4-dichlorophenyl)-4-methoxyimino-butanoic acid |
| 3 | 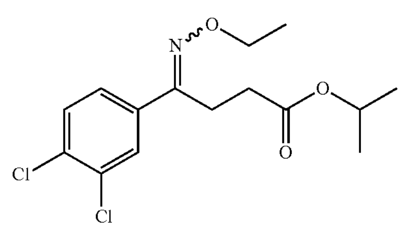 [SMILES: CCON=C(CCC(=O)OC(C)C)c1ccc(Cl)c(Cl)c1] | Isopropyl acid 4-(3,4-dichlorophenyl)-4-ethoxyimino-butanoate |
| 4 | 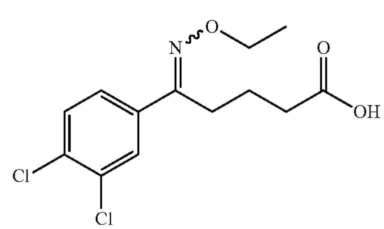 [SMILES: CCON=C(CCCC(=O)O)c1ccc(Cl)c(Cl)c1] | 5-(3,4-dichlorophenyl)-5-ethoxyimino-pentanoic acid |
| 5 | 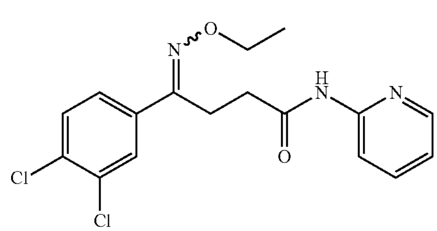 [SMILES: CCON=C(CCC(=O)Nc1ccccn1)c1ccc(Cl)c(Cl)c1] | 4-(3,4-dichlorophenyl)-4-ethoxyimino-N-(2-pyridyl) butanamide |

| No. | Chemical Structure | Chemical Name |
|---|---|---|
| 6 | 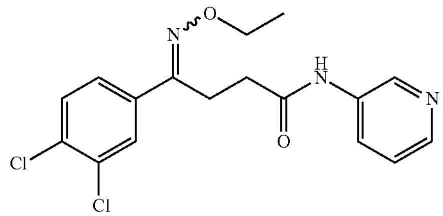 [SMILES: CCON=C(CCC(=O)Nc1cccnc1)c1ccc(Cl)c(Cl)c1] | 4-(3,4-dichlorophenyl)-4-ethoxyimino-N-(3-pyridyl) butanamide |
| 7 | 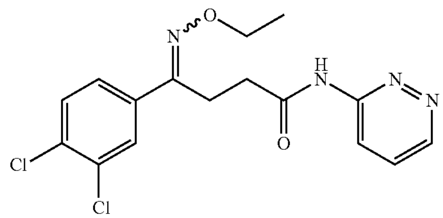 [SMILES: CCON=C(CCC(=O)Nc1cccnn1)c1ccc(Cl)c(Cl)c1] | 4-(3,4-dichlorophenyl)-4-ethoxyimino-N-pyridazin-3-yl-butanamide |
| 8 | 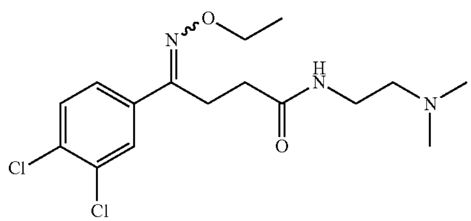 [SMILES: CCON=C(CCC(=O)NCCN(C)C)c1ccc(Cl)c(Cl)c1] | 4-(3,4-dichlorophenyl)-N-(2-dimethylaminoethyl)-4-ethoxyimino-butanamide |
| 9 | 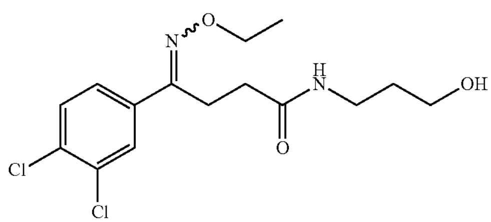 [SMILES: CCON=C(CCC(=O)NCCCO)c1ccc(Cl)c(Cl)c1] | 4-(3,4-dichlorophenyl)-4-ethoxyimino-N-(3-hydroxypropyl) butanamide |
| 10 | 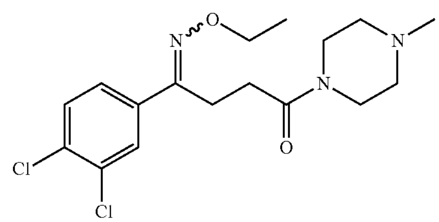 [SMILES: CCON=C(CCC(=O)N1CCN(C)CC1)c1ccc(Cl)c(Cl)c1] | 4-(3,4-dichlorophenyl)-4-ethoxyimino-1-(4-methylpiperazine-1-yl) butan-1-one |

As a matter of fact, patent application WO 2010011302 describes the synthesis of compounds 1 to 10 covered by the general formula (I) and their applications in the field of neurodegenerative diseases treatment without, however, describing activity on muscle atrophy. Thus, the inventors have surprisingly discovered that these known compounds have activity in the treatment and/or prevention of pathologies related to muscle atrophy in mammals.

In the context of this invention, the term "aryl group" means an aromatic ring having 5 to 8 carbon atoms or several fused aromatic rings having 5 to 14 carbon atoms. In particular, the aryl groups may be monocyclic or bicyclic groups, preferably phenyl or naphthyl. Advantageously it would be a phenyl group (Ph).

In the context of this invention, the term "heteroaryl group" means any aromatic hydrocarbon group of 3 to 9 atoms containing one or more heteroatoms, in particular one or two, such as, for example, sulfur, nitrogen or oxygen atoms, in particular, one or more nitrogen atoms. The heteroaryl according to this invention may consist of one or more fused rings. Examples of heteroaryl groups are furyl, isoxazyl, pyridyl, thiazolyl, pyrimidyl, pyridazinyl, benzimidazole, benzoxazole, benzothiazole, pyrazole. Advantageously, the heteroaryl group is chosen from pyridazinyl pyrazole and pyridyl groups.

In the context of this invention, the term "halogen atom" is understood to mean any halogen atom, advantageously chosen from Cl, Br, I or F, in particular chosen from F, Cl or Br, in particular F or Cl, more specifically, Cl.

In the context of this invention, the term "$C_1$-$C_6$ alkyl group" means any alkyl group of 1 to 6 carbon atoms, linear or branched, in particular methyl, ethyl, n-propyl, isopropyl, n-butyl, iso-butyl, sec-butyl, t-butyl, n-pentyl, n-hexyl. Advantageously, it is a methyl (Me), ethyl (Et), isopropyl (iPr) or t-butyl (tBu) group, in particular a methyl, ethyl or isopropyl group, more particularly a methyl or ethyl group.

In the context of the present invention, the terms "$C_3$-$C_6$ cycloalkyl group" means any saturated and hydrocarbon-based cycle comprising from 3 to 6 carbon atoms, in particular the cyclopropyl cyclobutyl, cyclopentyl or cyclohexyl group. Advantageously it is a cyclopentyl or cyclohexyl group.

In the context of this invention, the term "heterocyclic group" means any saturated cyclic hydrocarbon group of 3 to 9 atoms containing one or more heteroatoms, such as, for example, sulfur, nitrogen or oxygen atoms, in particular atoms of nitrogen and oxygen, more particularly one or more nitrogen atoms. The heterocyclic group according to this invention may consist of one or more fused rings. Examples of heterocyclic groups are tetrahydrofuran, tetrahydropyran, pyrrolidine, piperazine, piperidine, thiolane, oxirane, oxine, thiane, thiazolidine, morpholine groups. Advantageously, the heterocyclic group is chosen from tetrahydropyran, piperidine, pyrrolidine, piperazine and morpholine groups.

Within the scope of this invention, the term "pharmaceutically acceptable" is meant to be useful in the preparation of a pharmaceutical composition which is generally safe, non-toxic and neither biologically nor otherwise undesirable and which is acceptable for veterinary use as well as in human pharmaceuticals.

Within the scope of this invention, the term "pharmaceutically acceptable salts of a compound" means salts which are pharmaceutically acceptable, as defined herein, and which possess the desired pharmacological activity of the parent compound. Such salts include:
(1) acid addition salts formed with mineral acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid hydroxynaphthoic acid, 2-hydroxyethanesulfonic acid, lactic acid, maleic acid, malic acid, mandelic acid, acid methanesulfonic acid, muconic acid, 2-naphthalenesulfonic acid, propionic acid, salicylic acid, succinic acid, dibenzoyl-L-tartaric acid, tartaric acid, p-toluenesulphonic acid, trimethylacetic acid, trifluoroacetic acid and the like; or
(2) salts formed when an acidic proton present in the parent compound is replaced by a metal ion, for example an alkali metal ion, an alkaline earth metal ion or an aluminum ion; or coordinates with an organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

In the context of this invention, the term "solvate of a compound" is understood to mean any compound obtained by adding an inert solvent molecule to the compound according to the invention, the solvate being formed because of their mutual attractive force. The solvates are, for example, alcoholates of the compound. A hydrate is a solvate in which the inert solvent used is water. It can be a mono, di or trihydrate.

In the context of this invention, the term "tautomer" is intended to mean any constituent isomer of the compounds according to this invention which are interconvertible by the reversible chemical reaction known as tautomerization. In most cases, the reaction is produced by the migration of a hydrogen atom accompanied by a change of location of a double bond. In a solution of a compound capable of tautomerization, an equilibrium between the two tautomers is created. The ratio between the tautomers is then a function of the solvent, the temperature and the pH. The tautomerism is therefore the transformation of one functional group into another, most often by concomitant displacement of a hydrogen atom and a π bond (double or triple bond). Common tautomers are, for example, aldehyde/ketone-alcohol pairs or more precisely enol pairs; amides—imidic acids; lactams—lactims; imines—enamines; enamines—enamines. Ire particular, it may include a cycle-chain tautomerism that takes place when the movement of the proton is accompanied by the transformation of an open structure to a cycle.

The derivatives according to the invention can be administered in the form of a pharmaceutical composition comprising a pharmaceutically acceptable excipient.

These compositions may be formulated for administration to mammals, including humans. The posology varies according to the treatment and the condition in question. These pharmaceutical compositions are suitable for administration by any suitable route, for example orally (including buccal and sublingual route), rectally, nasally, topically (including transdermal), vaginal, intraocular or parenteral (including subcutaneous), intramuscular or intravenous). Advantageously, the pharmaceutical compositions are adapted for oral administration. These formulations can be prepared using any of the methods known to those skilled in the art by combining the active ingredients with the appropriate pharmaceutically acceptable excipients.

The unit forms of suitable oral administrations include tablets, capsules, powders, granules and oral solutions or suspensions in aqueous or non-aqueous liquids, comestible or edible foams, or liquid water-in-water emulsions or oil or oil-in-water. When preparing a solid composition in tablet form, the main active ingredient, advantageously in powder form, is mixed with a suitable pharmaceutical excipient such as gelatin, starch, lactose, magnesium stearate, talc, gum arabic or the like. The tablets may be coated with sucrose or other suitable materials or they may be treated in such a way that they will have prolonged or delayed activity and continuously release a predetermined amount of active ingredient.

A preparation in capsules is obtained by mixing the active ingredient, advantageously in powder form, with a diluent and pouring the resulting mixture into soft or hard gelatin capsules, in particular gelatin capsules. Lubricants such as, for example, talc, magnesium stearate, calcium stearate or polyethylene glycol in solid form can be added to the composition before it is filled into capsules. A disintegrant or solubilizer such as for example calcium carbonate or 0.15 sodium carbonate may also be added in order to improve the availability of the drug after taking the capsule.

In addition, suitable binders, lubricants and disintegrants as well as colorants may be added if necessary to the mixture. Suitable binders may be for example starch, gelatin, natural sugars such as for example glucose or beta-lactose, sweetening agents made from corn, synthetic or natural rubber such as acacia for example or sodium alginate, carboxymethylcellulose, polyethylene glycol, waxes and the like. Lubricants useful in these dosage forms include sodium oleate, sodium stearate, magnesium stearate, sodium benzoate, sodium acetate, sodium chloride, and the like. Disintegrants include starch, methylcellulose, agar, bentonite, xanthan gum and the like. The tablets are formulated for example by preparing a powder mixture, granulating or dry pressing the mixture, adding a lubricant and a disintegrant and pressing the mixture to give the tablets. A powder mixture is prepared by mixing the active ingredient suitably added with a diluent or a base and optionally with a binder such as, for example, carboxymethylcellulose, alginate, gelatin or polyvinylpyrrolidone, a dissolution retardant such as paraffin, an absorption accelerator such as, for example, a quaternary salt and/or an absorbent such as, for example, bentonite, kaolin or dicalcium phosphate. The powder mixtures can be, granulated by wetting with a binder such as for example a syrup, a starch paste, acacia mucilage or solutions of cellulose or polymeric materials and pressing them through a sieve. The granules may be lubricated by the addition of stearic acid, stearate salt, talc or mineral oil so as to prevent them from sticking to the molds used for manufacturing the tablets. The lubricated mixture is then pressed to produce the tablets. An opaque or transparent protective layer consisting of a shellac layer, a layer of sugar or polymeric materials may be optionally present. Dyes may be added to these coatings to differentiate them from other tablets.

A syrup or elixir preparation may contain the active ingredient together with a sweetener, an antiseptic, as well as a flavoring agent and a suitable colorant. In general, the syrup preparations are obtained by dissolving the compound in an aqueous solution with an agent giving an appropriate taste while the elixirs are prepared using a nontoxic alcoholic vehicle.

The water-dispersible powders or granules may contain the active ingredient in a mixture with dispersing agents or wetting agents, or suspending agents, such as, for example, ethoxylated isostearyl alcohols and polyoxyethylene sorbitol ethers, and with taste correctors or sweeteners. For rectal administration, suppositories are used which are prepared with binders that melt at rectal temperature, for example cocoa butter or polyethylene glycols.

For parenteral, intranasal or intraocular administration, aqueous suspensions, isotonic saline solutions or sterile and injectable solutions containing dispersing agents and/or pharmacologically compatible wetting agents are used.

The active ingredient may also be formulated as microcapsules, optionally with one or more additives.

The pharmaceutical compositions adapted for topical administration may be formulated as a cream, ointment, suspension, lotion, powder, solution, paste, gel, spray, aerosol or oil.

Pharmaceutical compositions adapted for nasal administration in which the excipient is in the solid state including powders having particle sizes for example in the range of 20 to 500 microns, administered by inhalation from a container holding the powder and placed near the nose.

Pharmaceutical formulations adapted for vaginal administration may be administered in the form of a buffer, cream, gel, paste, mousse or spray.

In an advantageous embodiment, the pharmaceutical composition according to this invention further comprises another active ingredient, advantageously having a complementary or synergistic effect.

This second active ingredient can be administered in the same pharmaceutical composition as the derivative of formula (I) of this invention. It may also be administered separately, either at the same time or over time.

The derivatives according to the invention are manufactured by methods that are well known to those skilled in the art and in particular the processes for preparing compounds 1 to 10 are described in the Prior Art (WO 2010011302).

The invention will be better understood in the light of the description of the figures and examples which follow, which are given by way of non-limiting description.

FIG. 1 shows the visualization of muscle fiber diameter (in μm) in the presence of the vehicle (control: Ctrl), of compound 1 at a concentration of 10 μM, with the dexamethasone (DEX) at a concentration of 10 μM, and IGF1 at a concentration of 10 ng/ml.

SCREENING CASCADE

The development of the screening test originated from the work of the literature and based on the characteristics of the pathology of Sarcopenia. At the pathophysiological level, this disease is characterized by a decrease in protein synthesis and an increase in proteolysis. Therefore, sorting out the abovementioned compounds was performed via tests that make it possible to evaluate the ability of chemical molecules to inhibit the gene expression of myostatin and their capacity to increase protein synthesis in muscle cells. In addition, we have shown that some of the products listed above increase the diameter of the myotubes in C2Cl2 cells.

Protocols:

Measurement of Myostatin Expression in C2Cl2

C2Cl2 myoblastic cells (ATCC CRL-1772) are seeded in 24-well plates at the density of 30,000 cells per well and cultured in DMEM (Dulbecco's Modified Eagle Medium) medium containing glucose at 4.5 g/L and supplemented with fetal calf serum (10%) and antibiotics (penicillin and streptomycin). Forty-eight hours later, the myoblasts are differentially induced by partial deprivation in serum (2% instead of 10%) for 5 days. The cells are then placed in a glucose-depleted medium (DMEM containing 1 g/L of glucose) and devoid of serum in the presence of the test molecules or references (IGF-1 at a concentration of 100 ng/ml) for 6 h. At the end of the experiment, messenger RNAs (mRNAs) are extracted using standard phenol and chloroform methodology. Briefly, the cells are lysed in a solution of trizol (Sigma T9424) containing a strong acid and phenol. The mRNAs are separated from the proteins by the addition of chloroform followed by centrifugation. They are then precipitated in isopropanol and then suspended at the concentration of 1 μg/μL in ultra-pure water free of RNA and DNA. 1 μg of mRNA is then converted by retro-transcription into complementary DNA by the AMV enzyme in the presence a primer and a mixture of nucleotides according to the protocol given by the supplier (Applied Biosystems 4368814). Gene expression is studied by polymerase enzyme-initiated chain reaction and commonly termed PCR under quantitative conditions, hence the precise name of qPCR. QPCRs are performed on a 79001-IT Fast Real-Time PCR detection system (Applied Biosystems). The programming conditions are standard and consist of 1 cycle at 95° C. for 15 min, followed by 40 cycles at 95° C. for 15 sec and 60° C. for 1 min and finalized with a melt curve step at 60° C. and 95° C. The analyzed samples all contain 100 ng of cDNA, a qPCR buffer including the enzyme, the mixture of oligonucleotides and the intercalating SYBR green, and the pair of specific primers of the gene being studied, strategically chosen between two exon sequences and at a final concentration of 200 nM. Fluorescent probes bind to the double-stranded. DNA and fluoresce only once attached to the DNA. A fluorescence threshold is established by the program of the machine. When the amount of DNA allows the fluorescent probe to exceed this threshold, a PCR cycle number called "Ct" is obtained for "cycle threshold" or cycle threshold. It is this value that is the basis of the calculations to quantify the DNA in a relative fashion. A ratio R is set between the amount of the starting DNA in a sample and that of a control, which has not been treated (i.e., $R=2^{-(Ct\ Sample - Ct\ Control)}$) and this measurement will be compared to that of a household gene known to be unmodulated by the treatment (or $R=2^{-\Delta\Delta Ct}$).

The primers used are recorded in the following table:
Primers Used to Evaluate the Modifications of Gene Expression

| Gene | Sequence 3'→5' | No. of Bases | Tm | Accession No. |
|---|---|---|---|---|
| Myostatin d | GAGTCTGACTTTCTAATGCAAG | 21 | 62 | Mouse: |
| Myostatin ind | TGTTGTAGGAGTCTTGACGG | 20 | 60 | NM_010834 |
|  |  |  |  | Rat: AF019624 |
| Atrogin d | AGAGTCGGCAAGTCTGTGCT | 20 | 62 | Mouse: |
| Atrogin ind | GTGAGGCCTTTGAAGGCAG | 19 | 60 | AF441120 |
|  |  |  |  | Human: |
|  |  |  |  | NM_058229 |
| Beta-actin d | CTCTAGACTTCGAGCAGGAG | 20 | 62 | Mouse: |
| Beta-actin ind | GGTACCACCAGACAGCACT | 19 | 60 | X03672 |

Protein Synthesis

The cells are counted and seeded at a density of 0.20000 cells per well in a 24-well plate in a DMEM medium containing glucose at 4.5 g/L and supplemented with fetal calf serum (10%) and antibiotics (penicillin and streptomycin). Forty-eight hours later, the myoblasts are differentially induced by partial deprivation in serum (2% instead of 10%) for 5 days. The cells are then placed in a medium without glucose or leucine (Krebs medium) for 1 hour at 37° C., and then incubated for 2 hours and 30 minutes in the presence of the test products or reference, (IGF-1, 100 ng/ml) in serum-free DMEM medium containing radiolabeled leucine 2.5 µCi/mL. At the end of the incubation, the supernatants are removed and the cells are lysed in a 0.1N NaOH solution for 30 min. The radioactivity is measured in the cell fraction and the total protein amount is determined by Lowry assay. Each condition is evaluated at a minimum of n=6; IGF-1, 100 ng/mL is our control to stimulate protein synthesis. The results are expressed in cpm/µg of proteins after 2.5 hours of incubation or as a percentage with respect to the control condition.

Evaluation of Muscle Fiber Diameter

The C2Cl2 myoblastic cells (ATCC CRL-1772) were seeded into glycerol-treated 8-well plates at a density of 10,000 cells per well and cultured in a DMEM medium containing glucose at 4.5 g/L and supplemented with fetal calf serum (10%) and antibiotics (penicillin and streptomycin).

Forty-eight hours later, the myoblasts are differentially induced by partial deprivation in serum (2% instead of 10%) for 3 days. The cells are then placed in a glucose-depleted medium (DMEM containing 1 g/L of glucose) and devoid of serum in the presence of the test molecules or references (IGF-1 at the concentration of 10 ng/mL or dexamethasone 10 nM) for 3 days. At the end of the culture, the cells are rinsed and fixed with 2.5% glutaraldehyde/0.1% Triton solution for 1 hour at room temperature. The cell layer is covered with DAPI (fluorescent labeling of the cell nucleus). After storage in the dark for 16 hours in the cold, the slides are observed under a fluorescence microscope (Carl Zeiss, AxioVert 200) and the images are analyzed using the Axiovision 4.1 software to measure the diameter of the fibers.

Results:

Effects on Myostatin Expression (Table 1)

For the effects on myostatin expression, the results are expressed as a percentage of myostatin gene expression in cells in contact with the molecules related to the expression in the control cells. The product is supposed to be active if this ratio is less than or close to 70%, the average, value of IGF-1 found at the concentration of 100 ng/mL in this test, considered as reference.

TABLE 1

| Number of the Compound | Concentration of the Compound 0.5 µm |
|---|---|
| 1 | 71% |
| 3 | 41% |

Compounds 1 and 3 significantly inhibit the expression of myostatin.

Effects on Protein Synthesis Via Phosphorylation of S6K1 (Table 2)

For the effects on protein synthesis, the results are expressed as a percentage increase in 56K phosphorylation in muscle cells. This percentage is considered significant when it is greater than 120%, the observed average value of IGF-1 at the concentration of 100 ng/mL in this test, considered as reference.

TABLE 2

| Number of the Compound | Protein Synthesis | | |
|---|---|---|---|
|  | 0.5 µm | 5 µm | 50 µm |
| 1 | 134% | 142% | 151% |

Compound 1 significantly increases protein synthesis in muscle cells at a concentration of 0.5 µM.

Effect of Compound 1 on Muscle Fiber Diameter (FIG. 1)

C2Cl2 cells are differentiated and treated with compound 1 for the last three days of differentiation. The results are shown in FIG. 1.

As expected, treatment with IGF-1 significantly increases the diameter of myotubes and in contrast dexamethasone significantly decreases this parameter. The diameter of the myotubes is significantly increased after treatment with compound 1 (FIG. 1).

BIBLIOGRAPHY

Bass J et al., Domest Anim Endocrinol, 1999, 17(2-3): 1991-197

Baumgartner R N et al., The journals of gerontology. Series A, Biological sciences and medical sciences 1998, 53(4): M264-74

Chai R J et al., PLoS One 2011, 6: e28090

Farnfield M M et. al., application. Physiol Nutr Metab 2012, 37:21-30

Frontera W R et al., Journal of applied physiology (Bethesda, Md.: 1985) 1991, 71(2): 644-50
Hasselgren P O et al., Biochemical and. Biophysical Research Communications 2002, 290(1): 1-10
Lee S J. Immunol. Endocr Metab Agents Med Chem. 2010, 10:183-194
Léger B et al., Rejuvenation Res 2008, 11(1): 163-175
Li Z B et al., J. Biol. Chem. 2008, 283(28): 19371-19378
Lloyd B D et al, J Gerontol A Biol Sci Med Sci. 2009 May, 64(5): 599-609
McPherron A C et al., Proc. Natl. Acad. Sci. USA 1997, 94:12457-12461
McPherron A C et al., J Clin Invest. 2002, 109: 595-601
Morley J E et al., Current Pharmaceutical. Design 2007, 13(35): 3637-3647
O'Neill E D et al., Age (Dordr) 2010, 32: 209-22
Purintrapiban J et al., Comparative Biochemistry and. Physiology B-Biochemistry & Molecular Biology 2003, 136 (3): 393-401
Thies R S et al., Growth Fact. 2001, 18: 251-259
Wolfman N M et al., Proc. Natl. Acad. Sci. USA 2003, 100:15842-15846
WO 2010011302.

---

The invention claimed is:

1. A method of treating muscle atrophy in a mammal or promoting muscle growth in an exercising mammal, comprising administering to the mammal an effective amount of a compound of general formula I below:

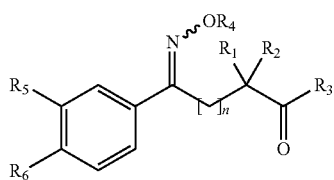

in which

R$^1$ and R$^2$ independently from each another are hydrogen or (C$_1$-C$_6$) alky;

n is an integer between 1 and 2;

R$^3$ represents an —OH group;

an —O(C$_1$-C$_6$ alkyl) group;

an —O (C$_3$-C$_6$ cycloalkyl) group;

an —O (C$_3$-C$_7$ heterocyclic) group;

an —O-heteroaryl group;

an —O-aryl group;

an —O(C$_1$-C$_6$ alkyl) aryl group;

an —NR$^7$R$^8$ group, in which

R$^7$ represents a hydrogen atom or a C$_1$-C$_6$ alkyl group and R$^8$ represents a hydrogen atom;

a heteroaryl group;

a C$_1$-C$_6$ alkyl group, optionally substituted with an —NR$^9$R$^{10}$ group in which R$^9$ and R$^{10}$ represent, independently of one another, a hydrogen atom or a C$_1$-C$_6$ alkyl group;

a C$_1$-C$_6$ alkyl group, optionally substituted with a group —OR$^{11}$ in which R$^{11}$ represents a hydrogen atom or a C$_1$-C$_6$ alkyl group;

or R$^7$ and R$^8$, together with the nitrogen atom to which they are attached, form a heterocycle, the heterocycle being optionally substituted with a C$_1$-C$_6$ alkyl group;

R$^4$ represents a hydrogen atom or a C$_1$-C$_6$ alkyl group;

R$^5$ and R$^6$ represent, independently from each other, a hydrogen atom, a halogen atom, or a group chosen from:

a —CN group;

an —OH group;

an —O(C$_1$-C$_6$) alkyl group, the alkyl group being optionally substituted by one or more halogen atoms;

a C$_1$-C$_6$ alkyl group, optionally substituted with one or more halogen atoms;

an —O(C$_3$-C$_6$ cycloalkyl) group;

or an enantiomer, diastereoisomer, hydrate, solvate, tautomer, racemic mixture or pharmaceutically acceptable salt thereof.

2. The method according to claim 1, wherein R$^5$ and R$^6$ represent independently from each other a halogen.

3. The method according to claim 2, wherein R$^5$ and R$^6$ are chlorine.

4. The method according to claim 1, wherein R$^4$ represents a C$_1$-C$_6$ alkyl group.

5. The method according to claim 4, wherein R$^4$ is ethyl.

6. The method according to claim 1, wherein n=1.

7. The method according to claim 1, wherein R$^3$ represents an —OH group or an —O(C$_1$-C$_6$ alkyl) group.

8. The method according to claim 7, wherein R$^3$ is —OEt or —OiPr.

9. The method according to claim 1, wherein R$^1$ and R$^2$ independently from each other are hydrogen or methyl.

10. The method according to claim 1, wherein R$^1$ and R$^2$ both represent a hydrogen atom.

11. The method according to claim 1, wherein the heteroaryl group of R$^7$ contains one or more nitrogen atoms.

12. The method according to claim 1, wherein the administered compound is at least one selected from:

(1) 4-(3,4-dichlorophenyl)-4-ethoxyimino-butanoic acid;

(2) 4-(3,4-dichlorophenyl)-4-methoxyimino-butanoic acid;

(3) Isopropyl 4-(3,4-dichlorophenyl)-4-ethoxyimino-butanoate;

(4) 5-(3,4-dichlorophenyl)-5-ethoxyimino-pentanoic acid;

(5) 4-(3,4-dichlorophenyl)-4-ethoxyimino-N-(2-pyridyl) butanamide;

(6) 4-(3,4-dichlorophenyl)-4-ethoxyimino-N-(3-pyridyl) butanamide;

(7) 4-(3,4-dichlorophenyl)-4-ethoxyimino-N-pyridazin-3-yl-butanamide;

(8) 4-(3,4-dichlorophenyl)-N-(2-dimethylaminoethyl)-4-ethoxyimino-butanamide;

(9) (4E)-4-(3,4-dichlorophenyl)-4-ethoxyimino-N-(3-hydroxypropyl) butanamide; and

(10) 4-(3,4-dichlorophenyl)-4-ethoxyimino-1-(4-methylpiperazin-1-yl) butan-1-one.

13. The method according to claim 1, wherein the mammal is human.

* * * * *